US008882652B2

(12) United States Patent
Vitzthum

(10) Patent No.: US 8,882,652 B2
(45) Date of Patent: Nov. 11, 2014

(54) (PARTIAL) APPARATUS FOR PREVENTING INCONTINENCE WITH A FIXING DEVICE TO BE IMMOVABLY IMPLANTED IN BODY TISSUE

(75) Inventor: Thomas Vitzthum, Ludwigsburg (DE)

(73) Assignee: R & M Consulting and Trading GmbH & Co. KG (DE)

( * ) Notice: Subject to any disclaimer, the term of this patent is extended or adjusted under 35 U.S.C. 154(b) by 819 days.

(21) Appl. No.: 12/928,954

(22) Filed: Dec. 24, 2010

(65) Prior Publication Data

US 2012/0165600 A1  Jun. 28, 2012

(51) Int. Cl.
*A61F 2/02* (2006.01)
*A61F 2/00* (2006.01)

(52) U.S. Cl.
CPC ...................................... *A61F 2/004* (2013.01)
USPC ......... 600/30; 600/29; 623/23.64; 623/23.67; 128/897; 128/898; 128/899

(58) Field of Classification Search
USPC .................. 600/29, 30, 32; 623/23.64, 23.67; 128/897–899, 885, 887; 604/337
See application file for complete search history.

(56) References Cited

U.S. PATENT DOCUMENTS

| 5,064,434 | A | * | 11/1991 | Haber | 623/23.67 |
| 5,498,240 | A | * | 3/1996 | Bagaoisan et al. | 604/96.01 |
| 6,033,390 | A | * | 3/2000 | von Dyck | 604/332 |
| 6,740,029 | B2 | * | 5/2004 | Rogers et al. | 600/37 |
| 6,802,808 | B2 | * | 10/2004 | Brady | 600/29 |
| 7,025,791 | B2 | * | 4/2006 | Levine et al. | 623/23.64 |
| 7,347,866 | B2 | * | 3/2008 | Daignault et al. | 606/191 |
| 2002/0151763 | A1 | * | 10/2002 | Cook et al. | 600/31 |
| 2002/0177902 | A1 | * | 11/2002 | Rioux et al. | 623/23.67 |
| 2004/0030217 | A1 | * | 2/2004 | Yeung et al. | 600/31 |
| 2004/0064014 | A1 | * | 4/2004 | Melvin et al. | 600/37 |
| 2004/0249343 | A1 | * | 12/2004 | Cioanta | 604/113 |
| 2005/0027161 | A1 | * | 2/2005 | Cook et al. | 600/31 |
| 2009/0299334 | A1 | * | 12/2009 | Nishtala et al. | 604/528 |

* cited by examiner

*Primary Examiner* — Christine Matthews
*Assistant Examiner* — Sunita Reddy
(74) *Attorney, Agent, or Firm* — Adams & Wilks

(57) ABSTRACT

An apparatus for preventing incontinence includes a tubular body with a first guiding element connected to a tube-shaped retaining element with a second guiding element that opens axially into a termination on a side of the retaining element. The retaining element is formed of a reversible stretchable and compressible metal grille that is air-tight and fluid-tight at the termination in a region of a transition thereof to the tubular body. A fixing device that fixes the apparatus when the apparatus is immovably implanted in a body tissue of a patient is formed of the first guiding element defining areas with axially spaced projections. In a non-extended state, the projections are formed as slits protruding out of the surface of the first guiding element and, in an axially extended state, the projections are immovably implanted in the body tissue when the first guiding element is compressed in an axial direction.

20 Claims, 11 Drawing Sheets

(PARTIAL) APPARATUS FOR PREVENTING INCONTINENCE WITH A FIXING DEVICE TO BE IMMOVABLY IMPLANTED IN BODY TISSUE

BACKGROUND OF THE INVENTION

1. Field of the Invention

The present invention concerns an apparatus for preventing incontinence and a part of this apparatus which then interacts with a second part and features a fixing device for immovable implantation in body tissue. The part of the apparatus which is to prevent incontinence features a tubular body with a first longitudinal guiding element inside. Connected to the tubular body is a tube-like retaining element which features a second elongated guiding element inside. This ends in a finish in an axial direction on its opposing side to the tubular body. The tube-like retaining element is formed as a reversible stretchable and compressible metal grid which features a polymer covering, together with which it is kept air- and liquid-tight at the finish on the one hand and in the vicinity of the transition to the pipe-like body on the other.

2. Background Information

The term incontinence basically means the inability to retain something. In terms of the present invention this can, for example, be aconuresis. Such an involuntary urine loss is definitely a frequently occurring illness which can have various causes. The general term aconuresis is therefore just the generic term for very different types of illness which can be differentiated and defined by means of their causes. In addition to incontinence caused by stress and pressure, motoric and sensoric urge incontinence are also known. These should in turn be distinguished from obstructive overflow incontinence and functional overflow incontinence, supra-spinal and spinal reflex incontinence or extraurethral incontinence as further causes of incontinence.

With regard to stress incontinence, an apparatus for controlling bladder function manufactured by the Uromedica company has become known which basically consists of two small implantable balloons. These are implanted under the skin next to the bladder during a short surgical procedure. The expansion of the balloons should protect against involuntary urination by compressing the urinary bladder. The natural passing of water is thus not inhibited as the balloon size is set so that for the purposes of urination, normal bladder pressure is sufficient to cause the bladder to be emptied. It should still be possible for a doctor to modify the fill quantity of the two balloons after implantation.

An apparatus of this kind has become known through WO-A-98/56311. WO-A-98/56311 describes an expandable apparatus for preventing aconuresis in which a tubular guide or conduit is connected to a balloon whose circumference can be modified and which is therefore adjustable. The tubular guide penetrates the balloon axially in such a manner that the guide extends into and projects out of the balloon. The respective joints between the conduit and the balloon are sealed liquid-tight, for example with silicone. Instead of sealing with silicone or a comparable chemical or polymeric adhesive, ultrasonic welding is also disclosed as a possible sealing technique.

A first passage which runs through the pipe-shaped conduit in an oblong direction ends within the balloon and opens out inside the same. This passage serves to fill the balloon, for example with a liquid, and thus expand it according to requirements, or to withdraw fluid and thus reduce the size of the balloon.

A further passage may be provided which serves to insert the apparatus in the vicinity of the urethra in a human body. This passage accordingly ends with an opening at the end area of the guide which extends beyond the balloon and into the body. This passage's further opening in the guide is located in the area between the balloon and its proximal end.

For one thing, chemical compounds are specified as materials for the balloon which are themselves capable of forming a seal with the tubular guide in the areas of contact. Compounds such as cross-linked silicone gel, polyvinylpyrrolidone and karaya gum are named. In addition to the embodiment of the expandable apparatus with a first passage with which the balloon can be filled or emptied as already explained, WO-A-98/56311 also elucidates that the balloon wall can also be pierced with a coreless hollow needle and filled or emptied in this manner. A biologically compatible non-elastically restorable elastomer or an appropriate polymer mixture of polyurethane, polymers such as polyethylene, polytetrafluoroethylene (PTFE), polystyrene or polyetheretherketone (PEEK) are named as further materials for the balloon.

The balloon wall can additionally feature reinforcing structures. For this purpose, the balloon is double-walled and the reinforcing structure is situated in between the walls. It can consist of fibres made of polyester, nylon, polypropylene, polytetrafluoroethylene (like TEFLON) or other polymers which feature a high degree of hardness or a high hardness modulus. The fibres may form a net which is woven into a supporting structure which is arranged between the walls of the balloon. In one embodiment, the fibres can be less elastic than the wall itself.

The woven support structure then features a loose fibre weave to permit extension or diminution of the balloon walls.

On the other hand, the fibres of the reinforcing structure can also be mainly non-elastic and woven, whereby the fibres are then knotted to also permit expansion or contraction of the balloon walls.

The reinforcing structure also has the additional task of holding back particles let into the balloon which can be used to expand it in place of a fluid so that they cannot leak out into the vicinity of the balloon. The fibres woven into the support structure can be equipped with a waterproof ripstop function. This means that drops which may form when the hollow needle enters the balloon for filling or emptying can also be absorbed.

With regard to the particles which can be used instead of or together with a liquid to fill the balloon, WO-A-98/56311 cites various examples of particles which by nature of their size can be injected into the balloon by means of a hollow needle in order to then enlarge their diameter within the balloon so that the balloon is expanded. One example of such particles features a core with numerous arms pointing away from it. These particles pass through the hollow needle in a compressed state and expand after entering the balloon. Other such particles can feature a pipe-shaped, elongated structure in order to pass through the hollow needle. The elongated structure then subsequently prevents the particles from flowing back through the needle or the opening in the balloon which forms when the hollow needle is withdrawn.

Further embodiments of particles can consist of hydrophilic material such as polyvinylpyrrolidone, polyethylene glycol, carboxymethyl cellulose or hyaluronic acid which expands inside the balloon.

PCT/EP2010/003757 has made a further apparatus for preventing incontinence known with which instead of the balloon from the previously described state of the art, a tube-like retaining element in the form of a reversible expandable and compressible metal grille is deployed.

This metal grille features a polymer covering and is kept fluid- and watertight on a tubular body in the form of a tubular, flexible tube. The metal grille may feature a diamond pattern whereby the diamonds in a compressed state are formed as slits which preferably feature an extension in the longitudinal direction of the flexible tube of a tubular retaining element connected to the tubular body.

This tubular body serves mainly to bring the retaining element designated as a metal grille to the location in the urethra from which the bladder function can be effectively and practically controlled.

The pipe-shaped, flexible tube is formed as a fabric-reinforced and/or fabric-braided tube, whereby a single or multiple layer of fabric may be present. The pipe-shaped, flexible tube can also feature metallic reinforcement.

The tubular body in the form of a pipe-shaped, flexible tube can be made as a tubular shrink tube of at least one biologically compatible thermoplastic. The material is then preferably selected from polyolefines, polyvinylchloride, polyvinylidenfluoride, polytetrafluoroethylene and/or Viton. This tube and the tube-like retaining element with the metal grille then merge.

The pipe-shaped shrink tube can also feature metallic reinforcement. This metallic reinforcement and also the reversible expandable and compressible metal grille of the tube-like retaining element are then preferably formed as a sandwich between two plastic layers.

In addition, the tubular body can feature an anti-microbial silver coating or a coating of diamond-like carbon in one of its embodiments.

Unlike WO-A-98/56311, the apparatus for preventing incontinence disclosed in this PCT-application is not filled with a fluid or any other expandable polymeric material but with air at atmospheric pressure in the vicinity of the tube-like retaining element.

The tubular body features a first guiding element in the form of a flexible shaft approximately in its centre with spacers which retain the shaft in the tubular body. In the vicinity of its distal end, this flexible shaft ends in an actuator which for its own part features a mesh positioned distally at the end to permit manual adjustment of the apparatus or adjustment by means of a motor drive.

It is of essential importance for the success of an apparatus for preventing incontinence that the two parts of the apparatus originally precisely implanted in the vicinity of the urethra do not subsequently wander and thus cast doubt on the reliability of the apparatus.

According to PCT/EP2010/003757, fixation of the tubular body and thus of the entire apparatus at the implantation site is made possible in that this tubular body features fixing elements in the form of protrusions such as pimples (knobs), hooks and/or scale-like protrusions which protrude outwards on its surface. These can he formed on the tubular body at regular intervals, for example in rows, or also at irregular intervals, whereby they are generally formed with it in one piece.

Such an arrangement of protrusions of the aforementioned type on the outer circumference of the pipe-shaped body can indeed fulfill the desired retaining function and thus contribute to keeping the implant immovably at the desired position after the surgical procedure, but it has disadvantages during the implanting itself. The reason for this is that due to the protrusions, at least part of the mouldings such as pimples or hooks, the tubular body has a larger circumference which should be avoided if at all possible during a minimally invasive procedure.

On the other hand, with WO-A-98/56311 an expandable inter-vertebral spacer has been disclosed in a completely different technical area, namely that of vertebral column implants. Such inter-vertebral spacers are mainly required in case of a slipped disc if parts of the spinal disc obtrude into the vertebral canal, i.e. the space in which the spinal cord lies. This process causes considerable pain. Treatment is either conservative or, in serious cases, by means of a surgical procedure. The spinal disc is partly or completely removed in the process and a spacer is then introduced between the adjacent spinal discs into which bone grows in order to join both discs to one another in this manner. This leads to spinal stiffening at the site of the procedure. It was a major aim of the aforementioned state of the art to provide an inter-vertebral spacer which requires the minimum surgery possible and thus itself features as small a diameter as possible when implanted. For this reason, WO-A-98/56311 proposed an inter-vertebral spacer with an initial, smaller diameter which can be inserted in the area between the two affected discs and then expanded to a significantly larger diameter. This larger diameter can overlap the initial diameter by three to five times or even more. In this way, optimum filling of the inter-vertebral area is achieved by means of the radial expansion of the disclosed spacer in accordance with the aforementioned state of technology without, however, requiring a correspondingly major surgical procedure.

This is achieved by the aforementioned state of the art in that a small axial tube is provided which features a surface and a proximal and a distal end. The surface of the tube exhibits several slits which define at least two axially displaced extensions in such a way that the extensions extend out of the surface and create a geometry of an expanded spacer when the tube is compressed axially. These axially displaced extensions comprise at least three or four extensions which extend correspondingly from the tube in three or four different directions.

Applied to the inter-vertebral area such an axial tube means that it is first inserted into this inter-vertebral area and then significantly compressed in length, whereby extensions expand laterally in the aforementioned three or four different directions which significantly increase the circumference of the tube and thus fill the inter-vertebral area without a correspondingly large wound being caused by the surgical procedure.

Based on this state of the art, the object of the present invention is therefore to provide an apparatus for preventing incontinence which features the benefits of the apparatus as they are possible with PCT/EP2010/003757 and which simultaneously permits an immovable placement of both parts of the apparatus with the least possible side-effects and with a minimum of invasiveness.

SUMMARY OF THE INVENTION

This object is solved according to the present invention by an apparatus for preventing incontinence which consists of two parts and with which at least one part of the apparatus features a fixing device for immovable implantation in body tissue, with a tubular body and a first elongated guiding element inside, whereby a tube-like retaining element is connected to the tubular body which features a second elongated guiding element inside which ends in an axial direction on its opposing side to the tubular body, and whereby the tube-like retaining element is formed as a reversible stretchable and compressible metal grille which features a polymer covering together with which it is kept air- and liquid-tight at the opening on the one hand and in the vicinity of the transition to the tubular body on the other.

According to the present invention, at least this one part of the apparatus for preventing incontinence is characterised in that the first elongated guiding element defines areas with axially displaced protrusions, whereby in a non-extended state the protrusions are formed as slits which extend out of the surface of the guiding element in an axial direction to form the finished extensions when the first guiding element is compressed.

This particularly takes into account the fact that the requirements made of the outward-facing surface of the (partial) apparatus for preventing incontinence and the requirements of the precise fit of the implant can fundamentally conflict with one another. Whilst the aforementioned surface should be as smooth as possible to prevent irritation to the surrounding tissue, firm anchoring in the tissue is necessary on the other hand to prevent the apparatus from slipping out of place. This problem can be counteracted by means of the surface modification provided for according to the present invention through the extensions which are provided not on but inside the pipe-shaped body of the first elongated guiding element. In this way, the first elongated guiding element can fulfill its function of stabilising the tubular body and simultaneously of keeping the apparatus fixed in place in a very tissue-protective manner.

According to a preferred embodiment, the slits in the first elongated guiding element run mainly parallel to the axis of the first guiding element. In a compressed state, the protrusions which extend outside project approximately at right angles to the axis.

It is especially preferred that the first guiding element, including the protrusions formed upon it, is formed of a nickel-titanium alloy with a shape memory effect. Such a nickel-titanium alloy with a shape memory effect is, for example, commercially available under the brand name of Nitinol®.

The first elongated guiding element is preferably formed as a hollow body. If a rod adapted to the inside diameter of the hollow body which features a pre-defined curve is for its part adapted to the anatomy of the implantation site and is then inserted into the first guiding element according to a further embodiment of the part of an apparatus for preventing incontinence according to the present invention, this curve can be transferred to the first guiding element and thus to the tubular body.

The axially displaced protrusions can be displaced at an angle of approximately 90° to one another. The protrusions then extend outwards very distinctively. The axially displaced protrusions can also be displaced at an angle of approximately 45° to one another. In this way, the surface features a more pronounced fine structure which can be more tissue-protective and therefore preferred for certain indications during implantation. This kind of tissue-protective formation of the protrusions can, however, have a diminishing effect on local anchorage. The selection of the surface structure and thus one of the two aforementioned embodiments of displacement, 90° or 45° to one another, must therefore be weighed up carefully.

The protrusions which extend out of the surface of the first guiding element in an axial direction when the first guiding element is compressed, form shoulders and form an angle of a to one another. This is preferably variably adjustable. This can easily be achieved by compressing the first guiding element more or less strongly. The angle α formed will be correspondingly more or less sharp. Influence can also be exerted on the surface structure of the first guiding element in this way. A less sharp angle α causes a less strong manifestation of the surface structure and vice versa.

The fact that the tubular body is preferably formed as a pipe-shaped flexible tube made of at least one biologically compatible plastic or polymer, whereby its material is selected from polyurethane, polyetherblockamides, polyamides, latex, polyvinyl chloride and/or silicone means that it can reproduce the structure formed by the external protrusions and simultaneously prevent a possible injury hazard for the surrounding tissue due to the structure of the extensions.

With regard to the material, the polyetherblockamides (PEBA), which are available commercially under the brand name of PEBAX® are worthy of special mention. As thermoplastic elastomers, they are characterised by a lower density compared to other thermoplastic elastomers such as polyurethanes. In addition, they have outstanding mechanical and dynamic properties. They therefore demonstrate outstanding elasticity, impact and fatigue resistance.

Alternatively, the tubular body can be formed as a so-called shrink tube of at least one biologically compatible thermoplastic. The structure formed by the external protrusions can then also be well formed and a possible injury hazard for surrounding tissue simultaneously avoided due to the structure of the extensions.

Above all, thermoplastics such as polyolefins, polyvinyl chloride (PVC), polyvinylidenfluoride (PVDF), polytetrafluoroethylene (PTFE) and/or Viton are worthy of consideration. Viton® is the designation for a plastic which is available commercially from the DuPont company. If such a shrink tube is used, the tubular body and the tube-like retaining element can be joined practically seamlessly to the metal grille. No specific connection such as by means of a marker tape or a clamp connection needs to be provided for.

If the tubular body in the shrink tube material is additionally formed according to the so-called braiding process as a fabric tube with a metal lining, for example platinum interlacing, the fine metal wires can merge with the tube-like retaining element and thus end in the tube-like retaining element. Due to this, the metal grille is additionally beneficially reinforced in the area of the transition from the tubular body to the tube-like retaining element. Shrink tubes are available commercially in various embodiments. There is a choice of thin, medium and thick-walled tubes.

If the tubular body is formed of fabric-reinforced and/or fabric-braided flexible tubing and features a metallic reinforcement, it is also possible to form the metallic reinforcement as well as the reversible extendable and compressible metal parts of the tube-like retaining element as a sandwich between two layers of plastic. The metallic reinforcement and the metal grille can thereby merge.

The pipe-shaped flexible tube is preferably additionally provided with a hydrophilic coating. This hydrophilic coating increases the sliding properties of the tube surface which makes implantation easier on the one hand and contributes on the other to increasing the wear comfort of the implanted apparatus.

The tubular body may additionally feature an anti-microbial silver coating or a coating of diamond-like carbon. These coatings are wafer-thin and respectively serve to minimise colonisation by germs.

The tubular body can also be formed as a flexible fabric-reinforced and/or fabric-braided tube, whereby the fabric lining consists of one single or multiple layers.

Such fabric-reinforced and/or fabric-braided flexible tubes can be preferred in order to achieve improved transmission of energy. Mention should be made here of silicone tubes with a monofilament polyester braided lining. A peroxide-braided, monofilament polyester fabric can also be used. Other plastics such as PEBA are suitable instead of polyester. The fabric braiding can be a single or a multiple braided layer.

The tube-like retaining element filled with air at normal or atmospheric pressure is especially preferred. Many problems connected with the provision of an apparatus for preventing incontinence which provides a retaining element which can be filled with fluid can thereby be very simply solved. The pressure which the apparatus according to the invention, and the respective part of the apparatus according to the invention, is to exert on the urethra as per the anatomic circumstances of the patient in order to effectively prevent their incontinence is adjusted by extending or contracting the tube-like retaining element. This expanding or contracting has the effect of a spring in practice.

The metal grille of the tube-like retaining element can be formed as a diamond pattern, whereby in their compressed state the diamonds are formed as slits which feature an extension in the longitudinal direction of the flexible tube. The slits, and thus the diamonds of the metal grille, are especially preferably of different sizes. The stress loading on the grille material with regard to the re-adjustable and actively adjustable form of embodiment is thereby significantly reduced and the durability of the material is optimised as regards long-term use.

If the part of the apparatus according to the present invention is adjustable, the first elongated guiding element ends on its distally opposite side in an actuator and projects above this for the purposes of manual adjustment or for adjustment via connection to a drive motor.

As an alternative to manual adjustment without a motor it is equally possible to perform adjustment controlled by a magnet. This type of adjustment offers the advantage that it can be performed from outside via the skin without surgical intervention.

If the part of the apparatus according to the present invention is actively adjustable, the first elongated guiding element can be formed as a rack which is held inside the pipe-shaped body by the projections and can be moved mechanically by hand or motor-driven via a lifting mechanism.

The actively adjustable apparatus can be coupled with a movement, inclination, pressure and/or volume sensor and controlled by at least one of these sensors.

With sensor types deployable according to the present invention, the main external and internal factors for monitoring and control are made accessible which can influence the correct use or the functional efficiency of the apparatus for preventing incontinence. Both external factors such as barometric pressure and also internal factors such as those which are physiologically founded can, for example, be queried via the volume sensor.

All the named sensor types are already known within the field of medical technology and are deployed in various applications. It is advantageous that they are attached externally and therefore place no further strain on the implantation site.

Since the air column formed in the tube-like retaining element is at atmospheric pressure it is correspondingly exposed to fluctuations in air pressure. More extreme conditions such as air pressure whilst flying or at altitudes of at least 2000 metres can by all means cause a change. The monitoring of the apparatus according to the present invention or the respective part of the invention makes allowances for this. In the process, either all the aforementioned sensors can be deployed together or alternatively at least one or two of them selectively as befits the purpose.

The previously described embodiments of the apparatus according to the present invention, including the aforementioned variants, respectively concern a part of the apparatus for preventing incontinence. The finished apparatus features two identical or different parts of the parts of the apparatus introduced here. These are respectively implanted adjacent to the patient's urethra.

Each of the embodiments of the (partial) apparatus according to the present invention described can now be implanted in a human body in such a way that it is in duplicate or combined with another of the parts of the apparatus already described.

The finished apparatus for preventing incontinence can thus be constructed in different ways. One option is that two parts of the re-adjustable and/or actively re-adjustable variant as described in detail above are implanted adjacent to the patient's urethra and thus form the finished apparatus.

Another possibility is that one part of the apparatus concerns the re-adjustable and/or actively re-adjustable variant whilst the other part is selected in the form of the non-re-adjustable variant and that the two different parts are implanted adjacent to the patient's urethra to form the finished apparatus.

It is, of course, also possible that the finished apparatus features two parts of a non-re-adjustable variant of the apparatus according to the present invention.

BRIEF DESCRIPTION OF THE DRAWINGS

In the following the invention shall be explained in more detail by means of examples of embodiments and the enclosed drawing.

Shown in the drawing are.

DETAILED DESCRIPTION OF THE INVENTION

1. Embodiment: Adjustable Apparatus

Figure 1:
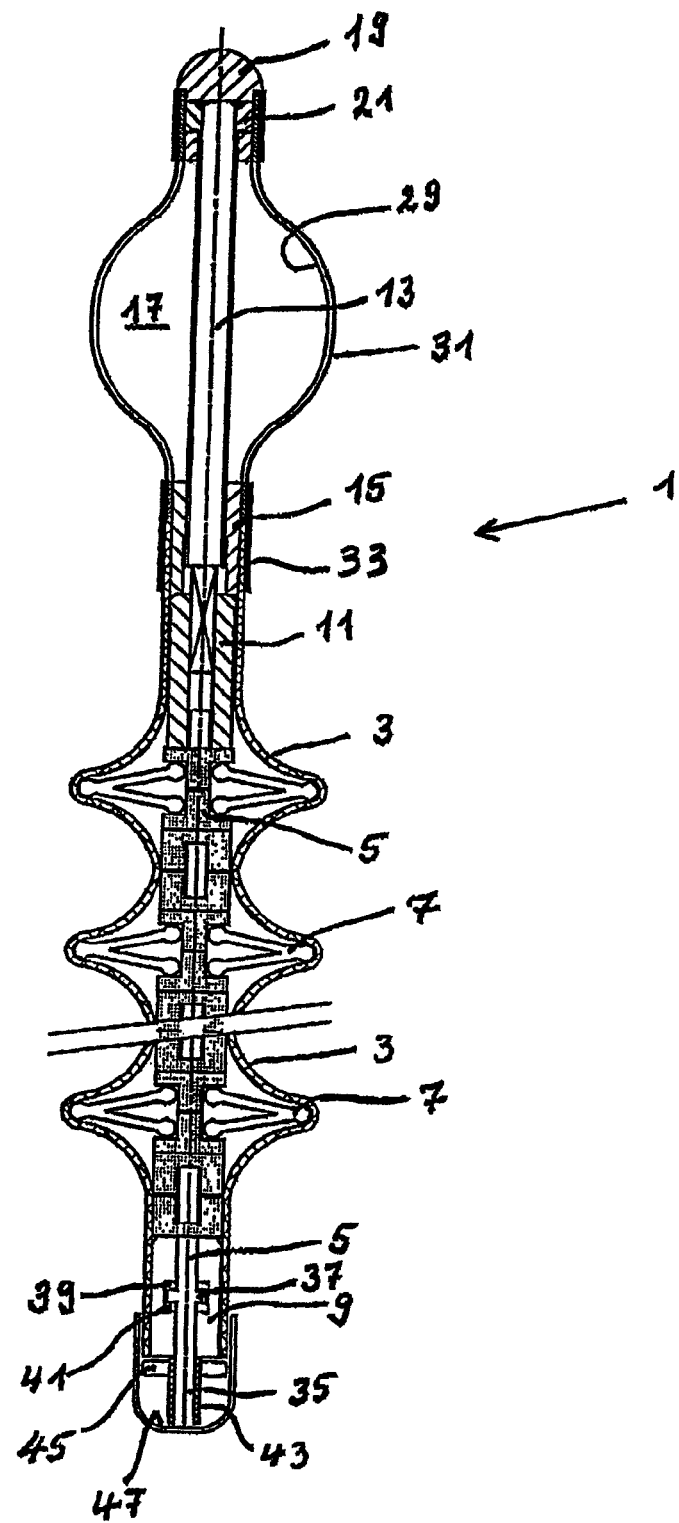
FIG. 1 a schematic cross-section view of an apparatus for preventing incontinence in a first embodiment, with a first elongated guiding element which features protrusions in an expanded state, FIG. 2 a schematic cross-section and incomplete view of the first elongated guiding element with slits, FIG. 3a a schematic perspective detailed view of two opposing externally protruding protrusions with a spacer, FIG. 3b a schematic cross-section detailed view of two opposing externally protruding protrusions with a spacer, FIG. 4 a schematic cross-section detailed view of an apparatus for preventing incontinence in a slightly curved embodiment and with additional re-adjustment, FIG. 5 a schematic cross-section view of the metal grille in non-expanded form as a detailed view as per Cut-out I of the adjacently depicted complete apparatus of the first embodiment example, FIG. 6 a schematic, cross-section detailed view of the apparatus according to the present invention which depicts the connection of the flexible tube to the intersection with the cage, FIG. 7 a schematic cross-section view of two adjustable (partial) apparatuses according to the present invention after transplantation into a body lumen, FIG. 8a a schematic cross-section and incompletely depicted view of an apparatus for preventing incontinence in a third, actively adjustable embodiment which displays the actuator as an adjustment mechanism, FIG. 8b a schematic cross-section detailed view of the apparatus according to the present invention as in FIG. 8a which displays the connection of the flexible tube to the intersection with the cage, FIG. 8c a schematic cross-section view of the apparatus according to the present invention with protrusions which are displaced axially at an angle of 45° to one another.

FIG. 1 shows an apparatus for preventing incontinence designated with the reference number 1 and one part of such an apparatus 1 which then in an implanted state is supplemented with a corresponding second part of apparatus 1; both these parts of apparatus 1 are then placed on each side of the urethra. For the sake of simplification, however, the one part of apparatus 1, which in fact represents just one part of the ready-to-use or prepared apparatus 1, is designated as the entire apparatus 1.

In its basic construction and functionality apparatus 1, as described hereinafter, corresponds to the same apparatus 1 as in the first embodiment of PCT/EP2010/003757, the disclosure of which is enclosed herewith by reference. The basic functionality of apparatus 1 in this first embodiment is, however, hereinafter described again, in order to subsequently explain the main modifications made to the invention.

Apparatus 1 correspondingly features a pipe-shaped body 3 which is formed as a flexible tube. Tubular body 3 is formed of a biologically compatible plastic or general polymer so that it can be implanted in a human body. A polyether block amide (PEBA) which is commercially available under the name of PEBAX®, latex, polyvinylchloride (PVC) and silicone have proven to be equally suitable during preliminary tests. It should therefore be clear to any person skilled in the art that these plastics and polymers represent examples of usable materials and that this should not be regarded as limiting. With regard to latex, it should be noted that in addition to natural rubber, synthetic rubbers are also suitable.

The same materials which were used in the first embodiment as per PCT/EP2010/003757 were tested in preliminary tests. What is new is that a silicone tube without further reinforcement was tested. A silicone tube in accordance with PCT/EP2010/003757 which featured a monofilament braided polyester lining was then used. In a further preliminary test, the same tube was used but with a platinum-braided embodiment. It was possible to achieve a hardness of approximately 70% Shore A with it.

A further preliminary test was performed with a peroxide-braided, monofilament polyester fabric as reinforcement for the silicone tube.

The reinforcement by the fabric lining and the platinum braiding had the purpose as per PCT/EP2010/003757 of making possible optimum transmission of energy. In this case this purpose no longer appeared to be a major focus for reasons still to be explained. However, since it is to be expected that the reinforcing fabric lining and the braiding can contribute to the longevity and resilience of apparatus 1 according to the present invention they were also tested as described. For this, it was necessary to test the elasticity of the aforementioned reinforcing materials.

All tests were completed with good results as regards the elasticity, durability and resilience of the tubes used. It was, however, ascertained that a simple silicone tube can also be used with the apparatus according to the present invention used here, in particular with the novel, modified design of the tubular body 3 which still has to be explained in detail in the following. This is of great benefit for cost reasons.

Unlike PCT/EP2010/003757, a different method is suggested to make the flexible tube which forms the tubular body 3 keep its shape following implantation in body tissue. According to the present invention it is thus possible to anchor the tubular body 3 and therefore the entire apparatus 1 firmly in place. Such local fixation means that the apparatus 1 does not move away from the site of implantation, either in the long-term or on account of short-term impacts.

In order to achieve such a firm anchorage, tubular body 3 features a first elongated guiding element 5, which due to the protrusions 7 formed upon it also simultaneously acts as a fixing device. This first elongated guiding element 5 in the form of the fixing device traverses practically the entire length of tubular body 3's flexible tube.

In the present embodiment the first elongated guiding element 5, including its protrusions 7, is formed of a nickel-titanium alloy which features super-elastic properties and a low elasticity modulus. For this type of alloy and its use as part of the first guiding element 5 according to the present invention, its elasticity and the exploitation of the form memory effect are decisive. This serves to give the protrusions 7 on the first guiding element 5 their form by the use of a force and to thus adjust them appropriately. This is explained thoroughly further below.

The first elongated guiding element 5 ends on its distally opposite side, i.e. with an intended implantation at end of the tubular body 3 facing away from the respective centre of the body in an actuator 9. Its function is also explained below, i.e. later, and not here, for reasons of clarity.

At its proximal end, i.e. the end facing the body of the implant wearer, the first elongated guiding element 5 ends in a coupling 11. This is an elastic coupling 11 made of an elastomer. The coupling 11 is beige elastic. It serves as a connecting element to a threaded rod 13 which is retained at the proximal end of the tubular body 3 by means of a threaded nut 15. The transition from the tubular body 3 to a cage altogether designated with the reference number 17 also takes place approximately at this location; this cage is formed in such a way that it can effectively prevent incontinence in a patient in conjunction with the tubular body 3. Threaded rod 13 passes through cage 17, which features air at normal pressure, and ends in a blanking plug 19 which seals cage 17 airtight and fluid-tight and simultaneously serves as the axial bearing for threaded rod 13.

After the main features of the basic design of apparatus 1 have been explained in this manner, the innovative design of the first elongated guiding element 5 in relation to PCT/EP2010/003757 is to be examined in more detail.

Tubular body 3 features the aforementioned protrusions 7 so that both parts of the apparatus for preventing incontinence remain at the location where they were implanted and do not, for example, wander within the body tissue due to the violent movements of the implant wearer. Their formation on the first elongated guiding element 5 are described in more detail below.

Figure 2:
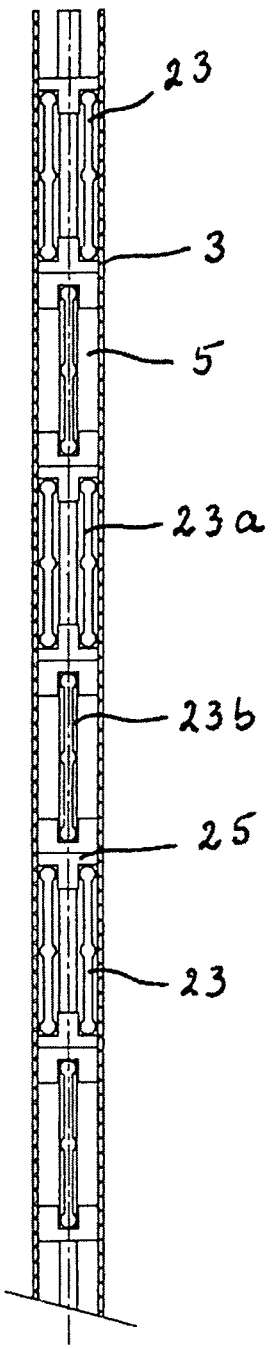
Figure 3A:
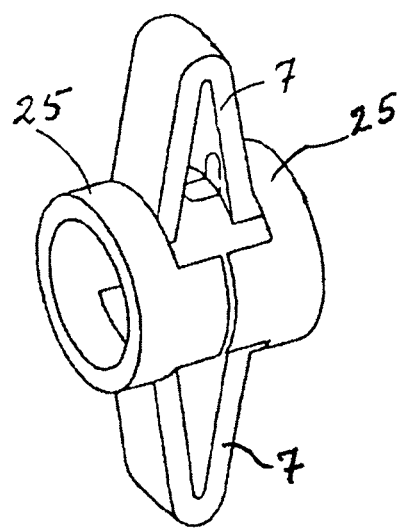
Figure 3B:
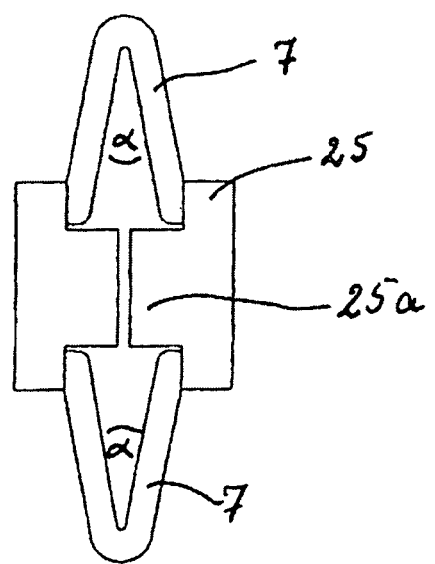

The first elongated guiding element 5 which shows protrusions 7 in a non-expanded state is depicted in FIGS. 3a and 3b. The first elongated guiding element 5 is a hollow body which, as shown in FIG. 2, initially features slits 23 at defined locations and at defined distances along its surface. For adequate fixing of the elongated guiding element 5 and thus the entire apparatus 1 it is of significance that areas 23a, 23b with different arrangements of the slits alternate which results in the different orientation of the protrusions. This alternation of the slit arrangements 23a, 23b is to be understood in that the slits 23 arranged in area 23a are displaced in an axial direction relative to the slits 23 arranged in area 23b. For the fixation of apparatus 1 it is sufficient if a total of three protrusions 7, but preferably four protrusions 7, are formed in the areas with different arrangements of the slits 23a and 23b.

If the two areas 23a and 23b feature a total of four protrusions 7, this means that as per this example of the embodiment that the protrusions 7 in the first area 23a are displaced 90° in an axial direction in relation to the protrusions 7 in the second area 23b. As can be seen from FIG. 2, areas 23a and 23b alternate along the length of the first elongated guiding element 5 insofar as slits 23a are provided on the first elongated guiding element 5 and protrusions 7 are to be formed accordingly.

In order to form protrusions 7 emanating from slits 23, the first elongated guiding element 5 is compressed in an axial direction. The protrusions 7 predefined by the formation of slits but not yet protruding from the surface of the tubular first guiding element 5 thus point or fold outwards and result in the completely erected protrusions 7.

In order to space these protrusions 7 in such a way that suitable anchoring for the apparatus 1 is formed in the respective body in which the apparatus 1 is implanted, partial areas 25 are provided which feature no slit and additionally spacers 25a by means of which the angle α at which the protrusions 7 protrude from the surface of the first elongated guiding element 5 can be adjusted. FIG. 3a shows a perspective detailed view of two opposing and externally protruding protrusions 7 for which spacer 25a increases the clearance between the shoulders of a particular protrusion 7 and thus the angle formed between the shoulders. FIG. 3b shows the same view but in cross-section so that here also the aforementioned angle α can be specified. Whilst the spacer 25a defines the clearance between two shoulders of one particular protrusion, the distance from the slit arrangement of the first area 23a to the slit arrangement of the second area 23b is defined by means of the partial areas 25. The distance between the slit arrangements of the first area 23a and the second area 23b is thereby selected in such a way that well-defined, distinguishable, pimple-like protrusions can form for the purposes of fixing the apparatus 1 for preventing incontinence. In this way a pimple-like, curved surface structure forms along the first elongated guiding element 5 which guarantees a firm seat for the apparatus 1 at the implantation site. Thereby the protrusions 7 are tissue-protectively expanded outside as rounded-off wedges.

Since the material from which the first elongated guiding element 5 is formed is a nickel-titanium form memory alloy as available commercially under the brand name of Nitinol®, and since special conditions therefore exist for material processing, these will be elucidated here in more detail. Nitinol® features a nickel content of some 50% and is up to 8% pseudo-elastically deformable.

For the processing of such a nickel-titanium form memory alloy it has proved to be especially propitious to cut the slits 23 in the tubular elongated guiding element 5 by means of laser technology. Amongst available laser techniques, special mention should in turn be made of cold material processing with which cutting with femtosecond laser pulses can be performed. Such a so-called cold material processing is possible with the StarFemto laser from ROFIN-BAASEL Lasertech GmbH & Co. KG, Starnberg, Germany. In addition, reference is made to the well-known technology of laser etching with which slits 23 can also be cut in Nitinol®.

On the basis of the selected material for a form memory alloy for the tubular first elongated guiding element 5 it is possible to provide a shape curved in the axis which makes it possible to take account of the local anatomical circumstances in the area of the urethra, i.e. the implantation site.

Two variants must be differentiated. On the one hand, the first elongated guiding element 5 can be formed to the desired curved shape before implantation in that the slits 23 for the protrusions 7 feature an unequal length which effect a curve on expansion. The first elongated guiding element 5 can, however, be formed into the desired curved shape in its expanded state by means of a flexible rod which is preformed to the desired curve. This is even possible after implantation, since the first elongated guiding element 5 is formed as a hollow body and the rod can then be bent and formed outside and then inserted.

Further experiments were performed with slits 23 for the protrusions 7 of unequal lengths. Areas 23a and 23b were provided with slits 23 which were cut or etched to unequal lengths on opposing sides so that the protrusions 7 extend in a different manner on compression, whereby one protrusion 7 is longer than the other opposing protrusion 7.

Figure 4:
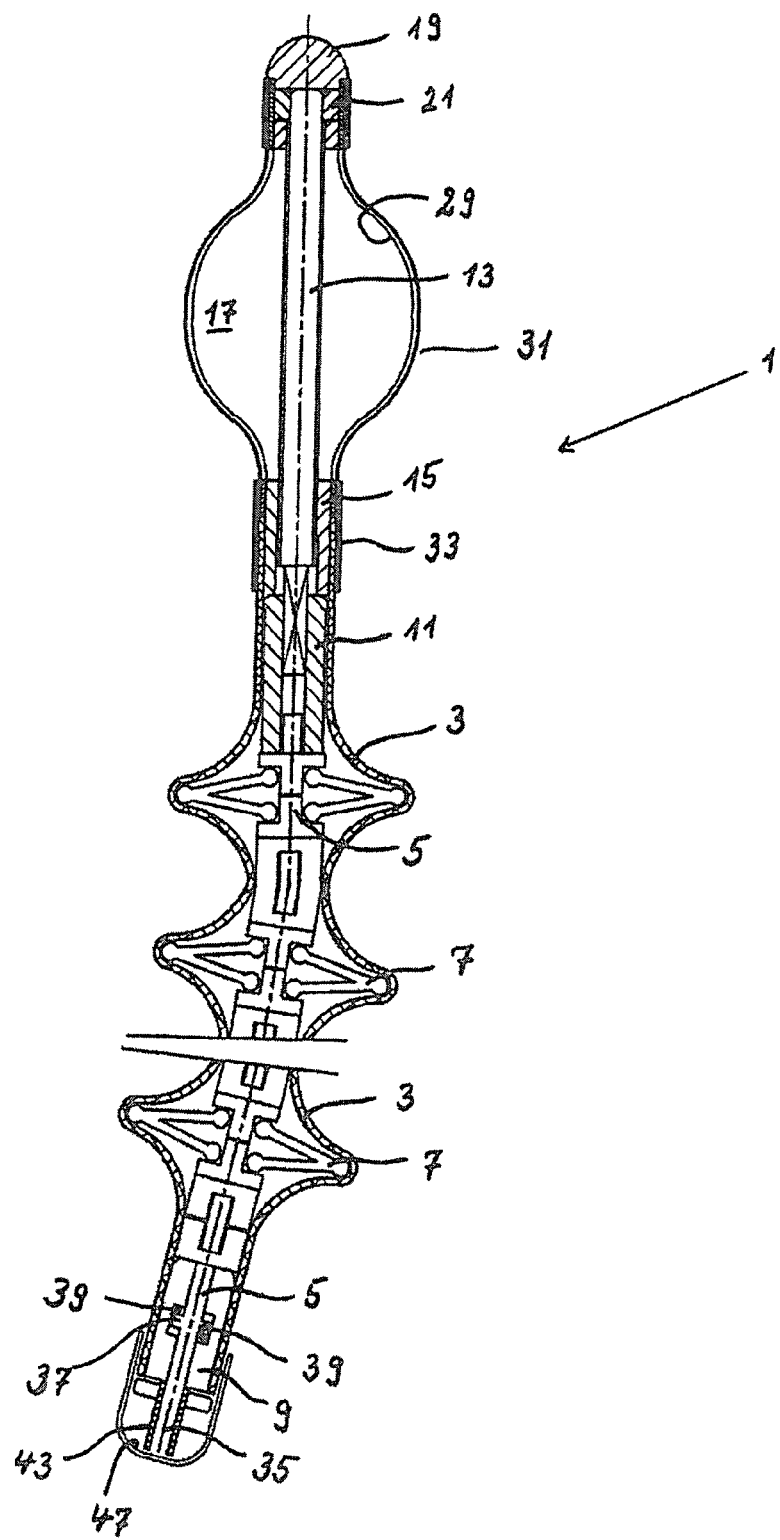

FIG. 4 shows an apparatus according to the present invention in a slightly curved form which additionally illustrates re-adjustment in situ, i.e. after implantation. This is to be dealt with in more detail below.

Re-adjustment of the apparatus 1 according to the present invention can be explained by means of a comparison of FIGS. 1 and 4. FIG. 1 and FIG. 4 basically show one and the same piece of apparatus 1.

The effect of a force still to be described in detail exerted on actuator 9 is shown which moves the first elongated guiding element 5 and thereby pulls the cage 17 slightly apart. The cage 17 is given a more elongated form compared to FIG. 1. If already implanted, this means that the pressure on the urethra, in the immediate vicinity of which the implant is located, is reduced. The effect exploited here can be approximately compared to a spring effect.

This illustrates a significant difference between the effect caused by adjusting the balloon fitted as a retaining element in the state of technology compared to adjusting the cage according to the present invention. Whilst the balloon according to the state of technology is basically filled with a liquid and is, for example, filled with more fluid or a comparable medium by means of a hollow needle in order to enlarge it, or fluid is removed by means of the hollow needle if a reduction in size is necessary, adjustment according to the present invention is performed by modifying an air column. The form of this air column is modified in that a force is applied to the actuator 9 which acts on the first elongated guiding element 5, moves it together with the coupling 11 and thus further elongates the cage 17—as seen in FIG. 4. A space or play 27 is created between the coupling 11 and the threaded nut 15.

This means that a force is exerted on the first guiding element 5 via the actuator 9 which has the effect of moving the first guiding element 5, which in turn acts on the cage 17 via the coupling 11 in such a way that it is extended. From comparing FIGS. 1 and 4 it is clear that the cage 17 in FIG. 4 features a more elongated form than was the case in FIG. 1.

Even if the cage 17, as it is used here, does not differ from the embodiment in PCT/EP2010/003757, so that reference can be made to the disclosure therein to the fullest extent, it is dealt with again in more detail below.

Figure 5:
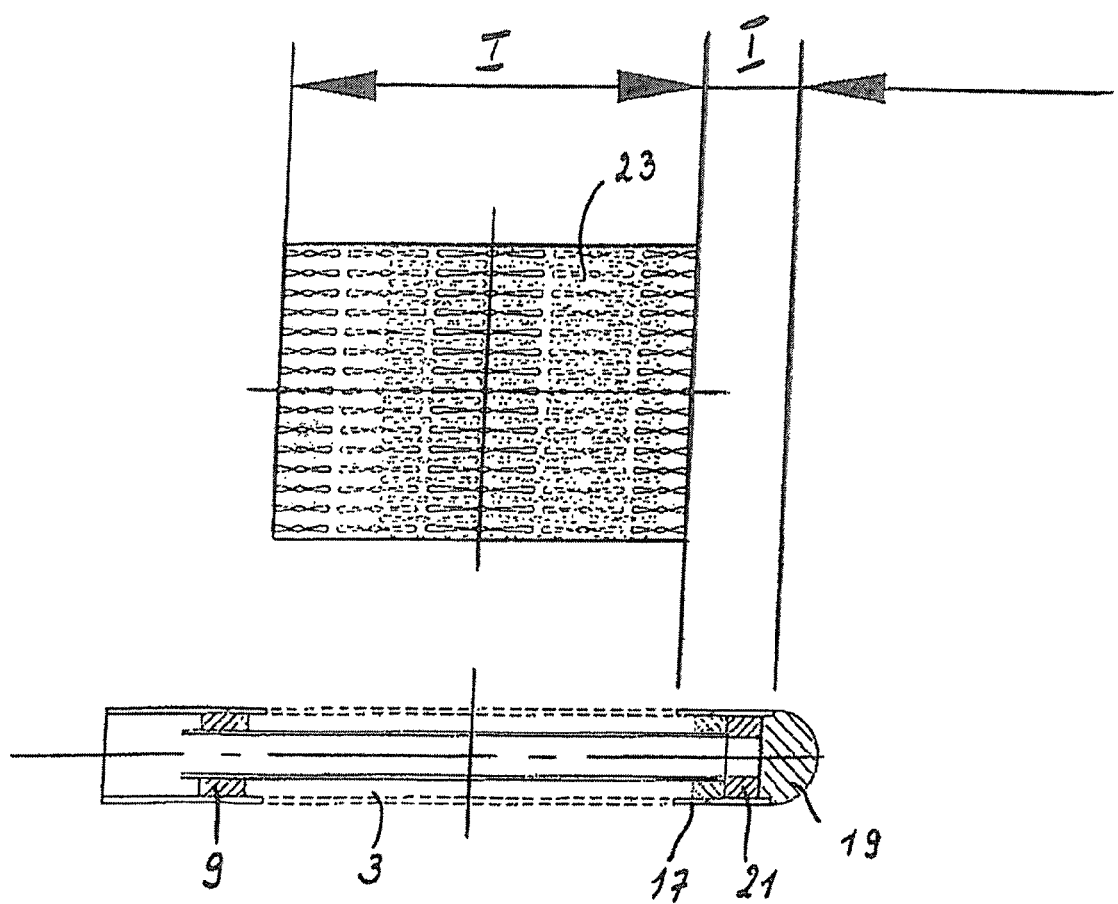

The cage 17 is formed of a fine metal grille 29 shown in FIG. 5, such has recently become known and is used for catheter procedures with metal grille stents in the field of carotid surgery. The metal grille 29 is formed with a diamond pattern because it needs to have the capacity for extending as required when the cage 17 expands. This means that by forming it to have the diamond pattern, the metal which is not extensible as such, but still does provide an extremely robust material, can be utilized because it makes possible an expansion-when the diamonds are extended- and a contraction- where the diagonal distances across the diamonds are reduced. In this manner, the metal material is rendered flexible.

FIG. 5 shows a sample cut-out of the cage 17 in non-expanded form with the entire apparatus 1 in non-expanded form shown once again adjacent to it. This depiction shows that the diamond-shaped grille structure is contracted together to form slits which extend along the length of the flexible tube 3. Experiments have shown that the effects of stress on the material can be optimised still further if the slits and thus the diamonds of the metal grille 29 are of differing sizes.

Figure 6:
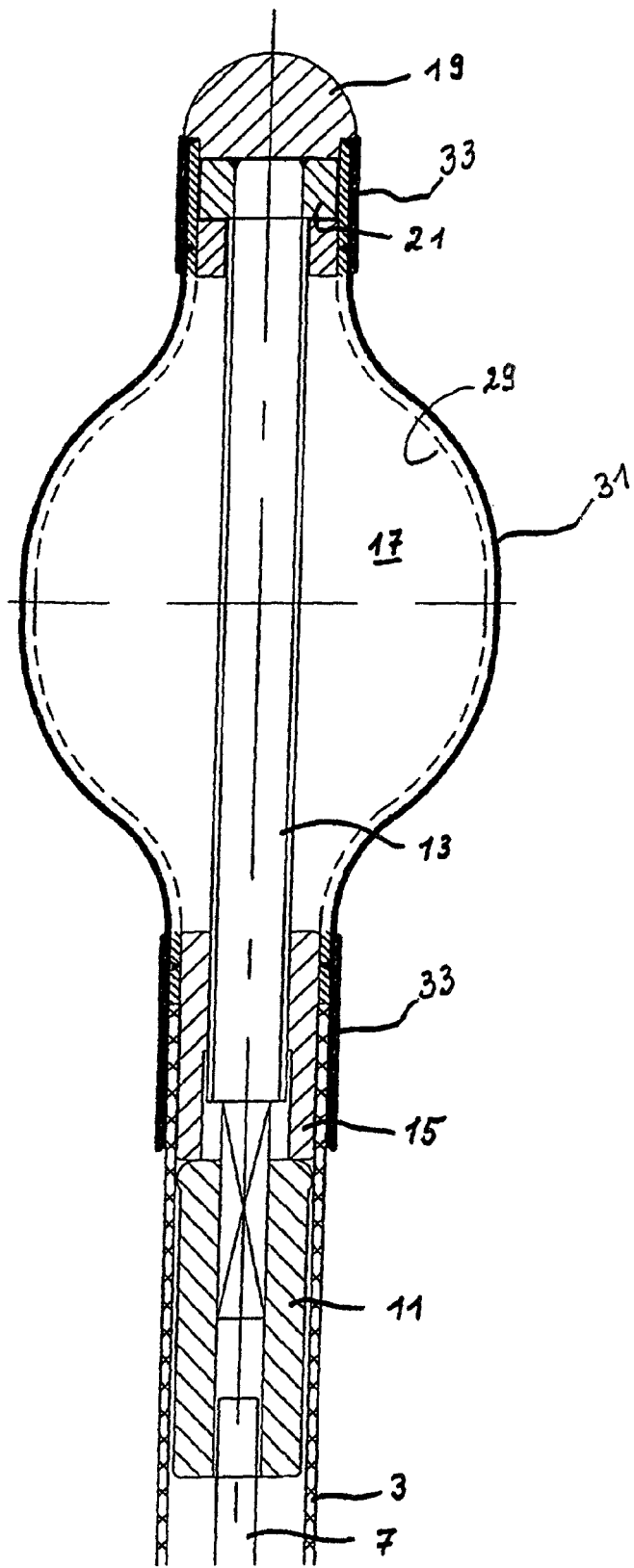

The metal grille 29 of the cage 17 is additionally coated air-tight and liquid-tight with plastic. In the embodiment in question this is achieved by a polymer covering or coating in the form of PTFE sleeve 31 which can be seen in FIG. 6 being pulled over the metal grille 29 and held in place by a marker tape attached to both sides of the sleeve and a clamp connection 33. The liquid-tight seal can, however, also be achieved by means of a silicone coating or a coating of the metal cage 17 with a comparable plastic.

The apparatus for preventing incontinence 1 according to the present invention as shown in FIGS. 1 and 4 and described in more detail here represents a re-adjustable apparatus 1 according to the present invention. Re-adjustment can be performed in different ways. In the simplest case, the first elongated guiding element 5 is moved back and forth manually so that the coupling 11 is moved and the cage 17 expanded or contracted.

In a further embodiment, the part of the apparatus 1 described here features a motor drive. The motor itself is not shown in FIG. 1.

Since the actuator 9 is a part of the apparatus for preventing incontinence according to the present invention which differs from the embodiments disclosed in PCT/EP2010/003757 this is to be explained in more detail below.

The flexible shaft inserted into the flexible tube of the apparatus for preventing incontinence as per PCT/EP2010/003757 ensures by means of a rotary movement that a force is exerted on the threaded rod situated inside the cage by means of a coupling at the opposing distal end. This can then be expanded or contracted lengthways.

In contrast, the first oblong guide element 5 is not turned according to the present invention but performs a linear movement in an axial direction. To achieve this, the actuator 9 has a different design compared to PCT/EP2010/003757. The first elongated guiding element 5 is fed through the actuator 9 at its distal end so that it projects with a section 35 in a distal position, i.e. on the outside. In the area in which the actuator 9 is fed through, the first elongated guiding element features no slits 23 which form the protrusions 7. In this area it is, however, fitted with elongated noses 37 which are formed on the surface and diametrically opposed to one another in such a way that they engage with almost complementary recesses 39 which are worked into the actuator 9. These recesses 39 are only insofar non-complementary to the noses 37 as these protrude in their length when regarded from an axial direction. Space to move or play 41 is thus created in an axial direction which generally permits the limited adjustment movements which can be necessary for the precise adjustment of the cage 17. It is unimportant whether this adjustment of the cage 17 is done manually or by means of a motor coupled to the section 35 which guarantees precise fine adjustment.

The section 35 of the first elongated guiding element 5 protruding past the actuator 9 in a distal position is fitted with a thread 43 on which a nut 45 is arranged. The first elongated guiding element 5 is held in place by the coupling 11 and this nut 45 attached to the actuator 9.

If the necessity of adjusting or re-adjusting the apparatus 1 according to the present invention consists of compressing cage 17 more strongly the nut 45 must first be loosened slightly. The first elongated guiding element 5 is inserted further into the flexible tube which is made possible by the play 41 in the recesses 39 on the actuator 9. This movement is transferred via the coupling 11 to the cage 17. The only limited play 41 in the recesses 39 on the actuator 9 simultaneously serves to ensure that unintentional stronger compression over and above what is acceptable is prevented. The nut 45 must possibly be slightly retightened after the cage 17 has been finally adjusted. This adjustment is possible manually and by means of a motor.

If the cage 17 is to be stretched, the first elongated guiding element 5 is carefully removed from the actuator. Here also, the only limited play 41 in the recesses 39 on the actuator 9 prevents expansion of the cage 17 over and above what is acceptable. In this case, the nut 45 has slight clearance after complete adjustment of the cage 17 and must be tightened accordingly. This adjustment is also possible manually or motor-driven.

A closing cap 47 is fitted on to the distal end of the apparatus 1 and thus secures it additionally. If necessary, the locking cap 47 features a socket 49 in its lid on the inside for the intervention of the distal end of the first elongated guiding element 5 including the nut 45.

Apart from this arrangement of the actuator 9 and its interaction with the distal end of the first elongated guiding element 5 which has been explained here as an example, further designs are possible which guarantee secure adjustment of the apparatus.

Figure 7:
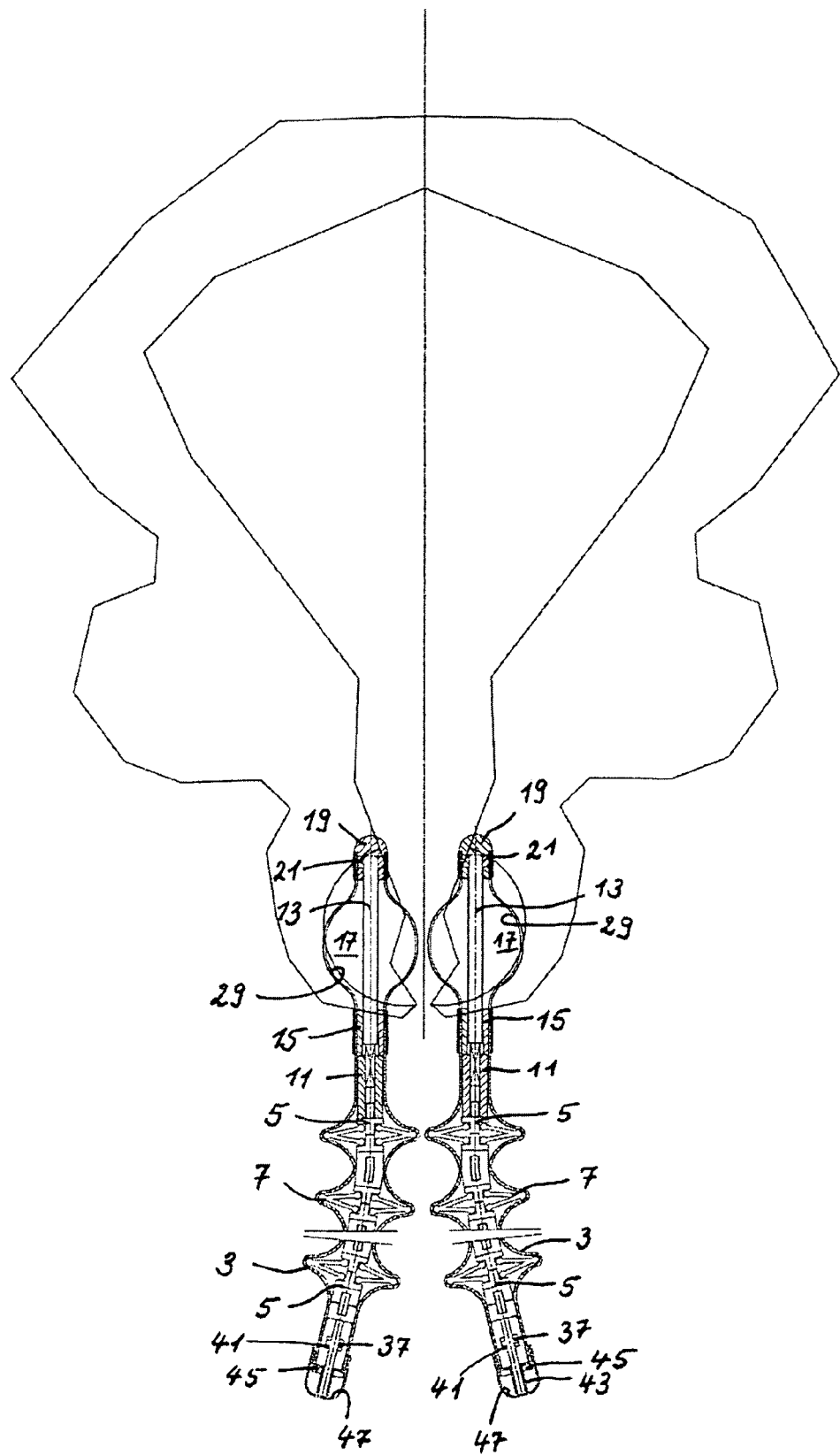

Implantation of the Apparatus According to the Present Invention in a Body Lumen in an Initial Variant FIG. 7 shows the implantation of the adjustable apparatus for preventing incontinence 1 according to the present invention in a body lumen. Two parts of the apparatus 1 are implanted opposite one another in such a manner that they hold the urethra of a patient suffering from incontinence centrally between them. The cage 17 in the embodiment described in the first embodiment above is filled with air. Just minimally invasive surgery is required to implant the two parts of apparatus 1.

If the two parts of the apparatus 1 are, for example, used in a male patient following a prostatectomy they are implanted directly in the vicinity of the operated urethra.

If the two parts of the apparatus are, for example, used in a female patient following a hysterectomy, they are implanted directly in the vicinity of the bladder.

The circumference of the cages 17 is chosen so that perfectly normal urination with normal bladder pressure is neither impaired nor partly or completely disabled when the parts of the apparatus 1 are in their final, i.e. adjusted position. The air columns in both cages 17 and their position next to the urethra are adjusted respectively by means of the first guiding element 5 proximally connected to the coupling 11 so that only indiscriminate urination, such as in the case of stress incontinence, is prevented. This can occur if the patient coughs, sneezes or has to make other comparable jerky movements. Lifting weights can also cause stress incontinence.

The cages 17 are precisely adjusted by means of the two different adjustment processes already described above, i.e. either manually or motor-driven. In both cases, the coupling 11 is moved back and forth over the first elongated guiding element 5 as required and the cage 17 is expanded or contracted in a very simple manner. Depending on the embodiment of the first elongated guiding element 5, this movement may also cause the protrusions 7 in relation to angle α, which form their shoulders, to extend somewhat as angle α is enlarged or compress somewhat if angle α becomes sharper so that they protrude further outwards. The movements required to adjust the size and extension of the cage 17 are in fact very small. The same applies to modifications of angle α of the shoulders of the protrusions 7. For manual operation, the nut 45 offers a good contact surface for a spanner of the correct size. The nut 45 can be inter alia a hexagonal or rectangular nut. A universal spanner can be used.

In case of motor-driven operation, a motor is connected to the apparatus 1 in the vicinity of the actuator 9 via the thread 43 of section 29, i.e., the distal end of the first elongated guiding element 5 protruding from the actuator 9. The first elongated guiding element 5 is then moved backward or forward as required with the coupling 11 by the motor and the cage 17 is extended or compressed in a simple manner as already described above. The first elongated guiding element 5 is then driven directly by means of the motor.

Magnetic valves which interact with an electro-magnet, cantilevers or piezo-actuator elements have all proved equally suitable for precise fine adjustment, whereby the latter are especially sensitive and permit especially good fine adjustment.

The procedure for adjusting both parts of the apparatus I according to the present invention is as follows: the parts are inserted in a minimally invasive surgical procedure and the wound initially left open for at least one day, which is not a problem in terms of minimally invasive surgery. The connection for the motor is implanted at the same time if required.

After both parts of the apparatus 1 have been reliably adjusted the nut 45 can be firmly aligned, the motor connection removed if necessary, the end cap 47 fitted and the wound closed.

2. Embodiment: Actively Operable, Adjustable Apparatus

Figure 8A:
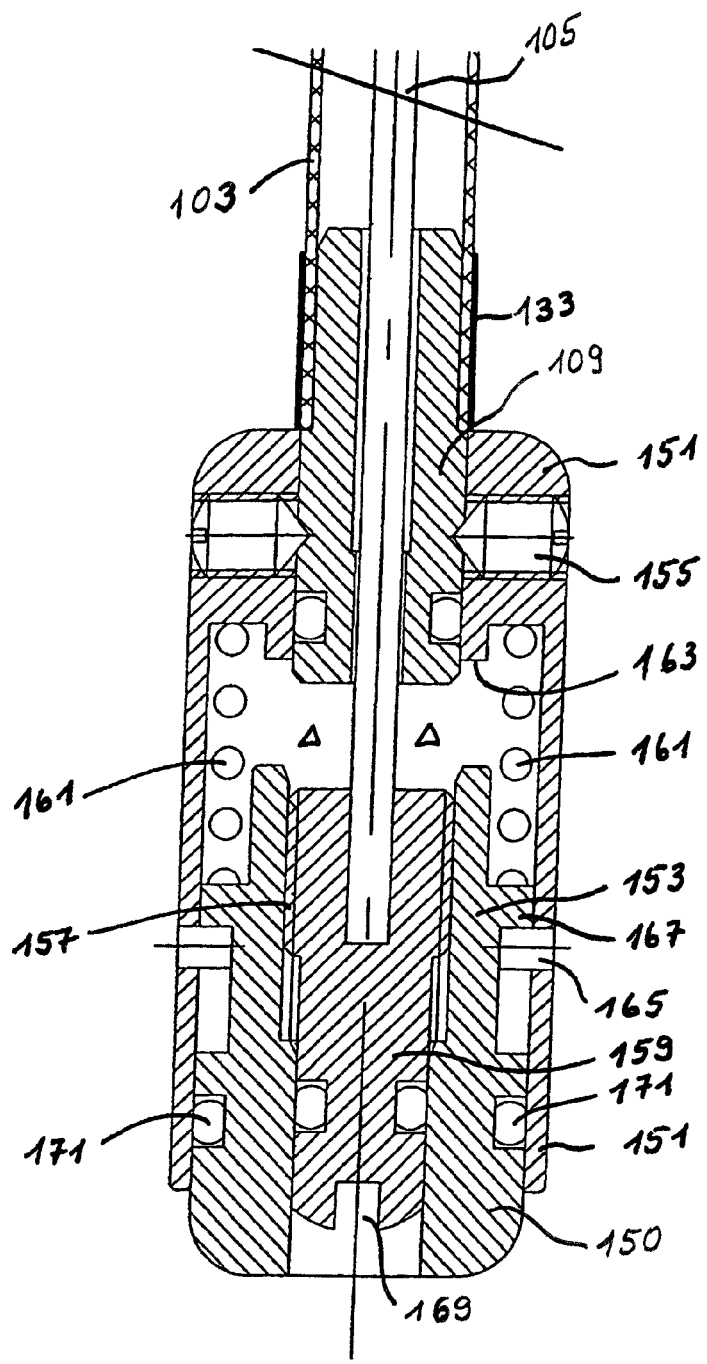
Figure 8B:
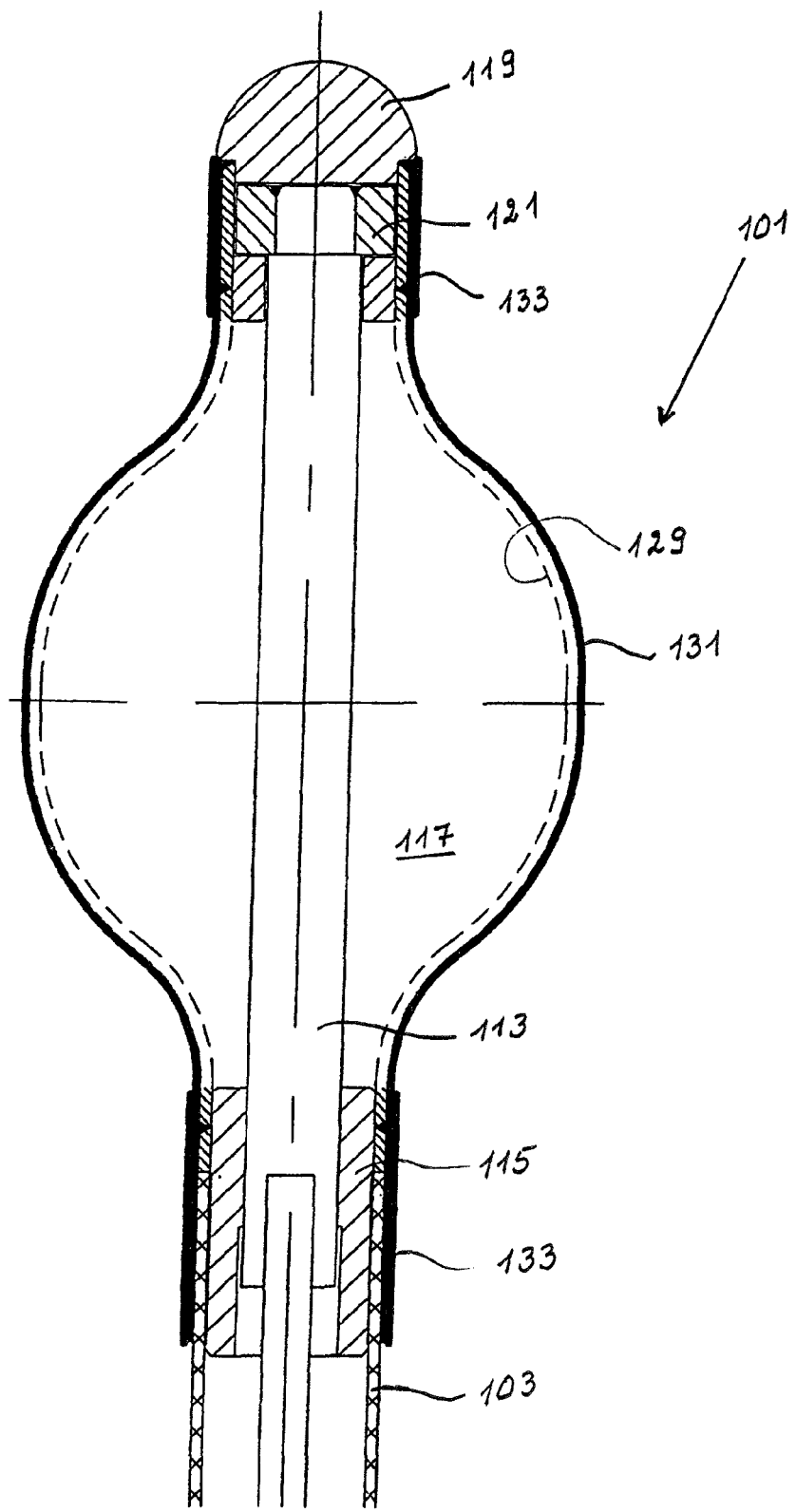
Figure 8C:
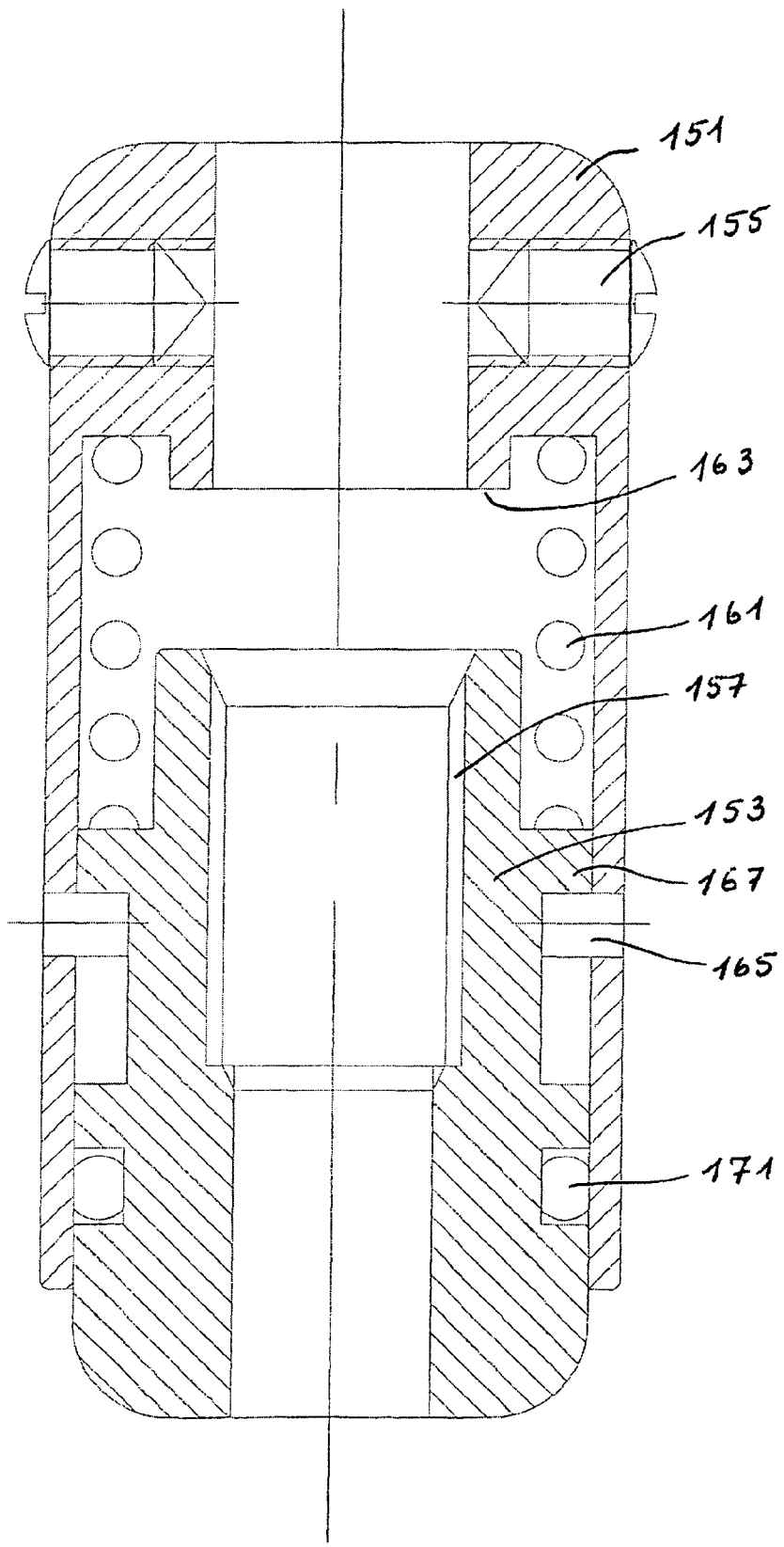

FIGS. 8*a* to 8*c* show a further embodiment of the apparatus for preventing incontinence according to the present invention which is and remains actively operable after implantation. These are the same components as in the first embodiment but with reference numbers offset by 100. The apparatus according to the present invention is accordingly designated the number 101.

The apparatus 101 again features a pipe-shaped, flexible tube 103 which is formed of a biologically compatible plastic or general polymer so that it can be implanted in the human body. Reference is made to the first embodiment in this respect.

In order to ensure it retains its shape, the flexible tube 103 features the first elongated guiding element 105 on which the protrusion are formed in the manner already described. The first elongated guiding element 105 is formed as a rack and ends at the distal end, i.e., the opposite end of the flexible tube 103 to the centre of the respective body in case of implantation in the actuator 109, which is formed as an adjustment device in this embodiment of the present invention which the patient in the vicinity of whose urethra the apparatus is implanted or the doctor treating the patient can operate post-operatively to re-adjust the apparatus.

The rack ends at its proximal end, i.e. the end facing towards the body, via the coupling (not shown in FIGS. 8*a* to 8*c*, but similar to coupling 11 in the first embodiment) in the threaded rod 113, which runs through the cage 117 and is retained at the proximal end of the flexible tube 103 by means of a threaded nut 115 as shown in detail in FIG. 8*b*.

The transition from the flexible tube 103 to the cage 117 has already been described in detail in the first embodiment to which reference is briefly made here. The sealing plug 119 closes the cage 117 air-tight and liquid-tight again and at the same time serves as an axial bearing 121 for the threaded rod.

In this embodiment, the plastic used to additionally cover the metal grille 129 of the cage 117 to make it air-tight and liquid-tight as described in more detail in embodiment 1 is a polymer covering or coating in the form of a PTFE sleeve 131, which is pulled over the metal grille 128 and held in place by a marker tape attached to both sides of the sleeve and a clamp connection 133. The airtight and liquid-tight seal can, however, also be achieved by means of silicone coating, for example, or a coating of the metal cage 117 with a comparable plastic.

The actuator 109 formed as an adjustment device for the apparatus for preventing incontinence 101 according to the present invention is described in more detail in the following as it is shown in FIGS. 8*a*-8*c*.

The actuator 109 formed as an active adjustment device is retained with its proximal end in the flexible tube at the distal end of the elongated guiding element 105. Marker tape attached to the outer circumference of the tube and a clamp connection 133 serves to retain the adjustment device. The aforementioned proximal end of the actuator 109 forms a guide 150 which accommodates the distal end, i.e., the end furthest from the body of the first elongated guiding element 105 formed as a rack and thus acts as its bearing.

The actuator 109 according to this embodiment also features an outer sleeve 151 which acts as a connection sleeve from the guide 150 with a piston 153 and is screwed to the guide 150 with screws 155, normally using 0-rings. The pre-tensioning of the cage 117 can be controlled axially via the screws 155. The piston 153 is connected to a fastener 159 by means of a thread 157 which accommodates the rack 105 in the vicinity of its distal end.

A generous amount of play is provided between the guide 150 and the fastener 159 which is bridged by return springs 161 and defines the path of the possible piston stroke.

If the piston 153 moves towards the cage, an end stop 163 inside the outer sleeve 151 limits the piston stroke in this direction. A pin inserted into the recess designated with the reference number 165 is provided to limit the piston stroke in the other direction and interacts with a corresponding protrusion 167 on the outer circumference of the piston 153 in that the pin forms an end stop for the protrusion 167. This prevents the guide 150 for the rack 105 in the actuator 109 which is connected to the piston 153 by a threaded connection from being pulled out of the outer sleeve 151 completely. Furthermore, sealing elements 171 ensure sufficient segregation of the inside of the actuator 109 from the outside.

A groove-shaped recess 169 is provided on the distal limit of the guide 150 connected to the piston 153 and thus accessible from outside which serves as an adjusting screw in order to be able to influence the pre-tensioning of the cage manually by means of a screwdriver.

Alternatively, with this embodiment a motor can be connected to the apparatus 101 by means of this distal area of the actuator 109 instead of manual post-operative adjustment by the patient themselves or by the doctor treating them.

The air column formed in the cage 117 which features the customary air pressure in this further, already described embodiment is subject to air pressure fluctuations. Longer test series have shown that these air pressure fluctuations normally only produce minor changes to the air column in the cage. Extreme or more extreme conditions such as air pressure changes when flying or at altitudes above 2000 metres can definitely cause a change.

Movement, inclination and/or pressure sensors have been additionally combined with the apparatus 101 according to the present invention. All three sensor types mentioned are already known in the field of medical technology and are used in various applications. Their benefit is that they are attached externally and therefore do not place further strain on the implantation site.

Optional placement of the sensors as required was also included in the preliminary tests. The use of just a pressure sensor has proven sufficient when flying in accordance with the preliminary tests. Under normal use it can be very convenient to use an additional movement sensor which, for example, takes into account the patient's resting phases and prevents re-adjustment in this time in which no signals are transmitted to the pressure sensor. The coupling of the sensors with one another is possible for a specialist in the art of current control engineering so that it does not need to be specifically mentioned in detail here.

Fully automatic re-adjustment is possible accordingly. Steps should in fact be taken to provide this so that it is not the patient who acts as an untrained operator of the apparatus 101 but an automatic device which finely adjusts via the motor and the adjusting screw. Regular checks by the attending doctor then round off the adjustment in a medically acceptable manner.

With the (partial) apparatus for preventing incontinence mentioned so far in one of its variants, the protrusions formed on the first elongated guiding element 105 were displaced relative to one another by an angle of approximately 90° respectively.

Figure 9:
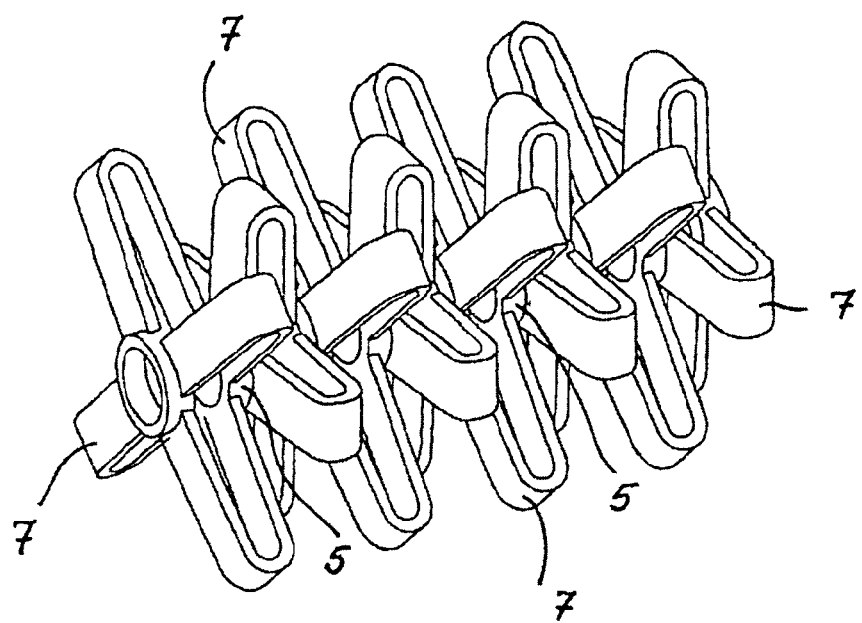
FIG. 9 is a perspective view of an embodiment of an elongated guiding element for an apparatus for preventing incontinence according to the present invention.

In contrast, FIG. 9 illustrates a first guiding element on which the protrusions 7 extending from the guiding elements 5 are formed in such a way that they are displaced at an angle of approximately 45° to one another respectively.

Both variants, an axial displacement of the protrusions to one another at an angle of 45° or 90°, both have their advantages depending on the anamnesis and the nature of the implantation site, so it should be weighed up as to whether a more pronounced extrusion of the protrusions or maximum tissue protection is to be achieved.

The invention claimed is:

1. An apparatus adapted to be immovably implanted in a body tissue of a patient for preventing incontinence in the patient, the apparatus comprising:
    a tubular body inside of which is a first longitudinal guiding element;
    a tube-shaped retaining element connected to the tubular body and inside of which is a second longitudinal guiding element that opens in an axial direction into a termination on a side of the tube-shaped retaining element, the tube-shaped retaining element comprising a reversible stretchable and compressible metal grille having a polymer coating so that the metal grille is air-tight and fluid-tight at the termination in a region of a transition thereof to the tubular body; and
    a fixing device for fixing the apparatus in a state in which the apparatus is immovably implanted in the body tissue of the patient, the fixing device comprising the first longitudinal guiding element defining areas with projections that are axially spaced relative to each other, the projections comprising slits which protrude out of a surface of the first longitudinal guiding element in a non-extended state of the projections and being configured to be immovably implanted in the body tissue of the patient in an axially extended state of the projections when the first longitudinal guiding element is compressed in an axial direction.

2. The apparatus according to claim 1, wherein the slits of the fixing device run mainly parallel to an axis of the first longitudinal guiding element.

3. The apparatus according to claim 1, wherein the first longitudinal guiding element is formed of a nickel-titanium alloy with a shape memory effect.

4. The apparatus according to claim 1, wherein the first longitudinal guiding element has a hollow body.

5. The apparatus according to claim 4, further comprising a rod inserted into the hollow body of the first longitudinal guiding element, the rod having a pre-defined curvature that is adapted to an anatomy of an implantation site corresponding to the body tissue of the patient in which the apparatus is implanted, the curvature of the rod being conferred onto the first longitudinal guiding element and onto the tubular body.

6. The apparatus according to claim 1, wherein the projections of the fixing device aligned at an angle of 90° to one another.

7. The apparatus according to claim 1, wherein the projections of the fixing device protrude axially from the surface of the first longitudinal guiding element and are configured so as to form flanks when the first longitudinal guiding element is compressed, the protrusions being positioned at a variably adjustable angle relative to one another.

8. The apparatus according to claim 1, wherein the tubular body comprises a pipe-shaped, flexible tubing made of at least one biologically compatible plastic or polymer material, the material being selected from among polyurethanes, polyetherblockamides, polyamides, latex, polyvinylchloride and/or silicone.

9. The apparatus according to claim 1, wherein the tubular body comprises a pipe-shaped shrink tube made of at least one biologically compatible thermoplastic material, the material being selected from among polyolefins, polyvinylchloride, polyvinylidenfluoride, and/or polytetrafluoroethylene; and wherein the pipe-shaped shrink tube and the tube-shaped retaining element with the metal grille fit into each other.

10. The apparatus according to claim 9, wherein the pipe-shaped shrink tube has a metallic reinforcement.

11. The apparatus according to claim 1, wherein the tubular body comprises a pipe-shaped flexible tube provided with a hydrophilic coating.

12. The apparatus according to claim 1, wherein the tubular body comprises a flexible, fabric-reinforced and/or fabric-braided tube with a single or multiple fabric insert.

13. The apparatus according to claim 1, wherein the tubular body has an antimicrobial silver coating or a coating made of carbon.

14. The apparatus according to claim 1, wherein the tube-shaped retaining element is filled with air at atmospheric pressure.

15. The apparatus according to claim 1, wherein the tubular body has a generally closed enveloping sheath formed on a surface of the tubular body, and outward-facing fastening elements comprising protrusions moulded on the tubular body and constructed in one piece with the tubular body.

16. The apparatus according to claim 15, wherein the protrusions are moulded on the tubular body at regular intervals in rows or at irregular intervals.

17. The apparatus according to claim 16, wherein the protrusions are moulded on the tubular body and comprise knobs, hooks, and/or protrusions.

18. The apparatus according to claim 1, wherein the apparatus is actively adjustable, and the tubular body has as the first longitudinal guide element a toothed rod which is held in the tubular body by spacers, the toothed rod being configured to be moved via a lifting device mechanically by hand or motor-driven.

19. The apparatus according to claim 18, wherein the actively adjustable apparatus is configured to be coupled to and controlled by at least one of a motion, inclination, pressure and/or volumetric sensor.

20. The apparatus according to claim 1, wherein the apparatus is adjustable, and the tubular body has as the first longitudinal guide element a flexible shaft disposed approximately in a middle of the tubular body and held therein by spacers; and wherein the flexible shaft opens at a distal end section thereof into an actuator having a slot at a distal end thereof for manual adjustment or for adjustment via connection to a motor as a drive unit.

* * * * *